US00PP16033P2

(12) United States Plant Patent
Olesen et al.

(10) Patent No.: US PP16,033 P2
(45) Date of Patent: Oct. 11, 2005

(54) ROSE PLANT NAMED 'POULFL001'

(50) Latin Name: ***Rosa* hybrid**
Varietal Denomination: PUOLfl001

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 64 days.

(21) Appl. No.: 10/813,531

(22) Filed: Mar. 29, 2004

(51) Int. Cl.[7] ..... A01H 5/00
(52) U.S. Cl. ..... Plt./151
(58) Field of Search ..... Plt./151, 150, 140

*Primary Examiner*—Anne Marie Grunberg
*Assistant Examiner*—June Hwu

(57) ABSTRACT

A new garden rose plant of the floribunda class which has abundant, red flowers and attractive foliage. This new and distinct variety has shown to be uniform and stable in the resulting generations from asexual propagation.

2 Drawing Sheets

Botanical classification: *Rosa* hybrid.
Variety denomination: 'POULfl001'.

SUMMARY OF THE INVENTION

The present invention constitutes a new and distinct variety of garden rose plant which originated from a controlled crossing between the female parent 'Tanlilida', a non-patented variety, and the male pollen parent, an unnamed seedling. The two parents were crossed during the summer of 1991 and the resulting seeds were planted in a controlled environment in Fredensborg, Denmark. The new variety is named 'POULfl001'.

The new variety may be distinguished from its female seed parent, 'Tanlilida' by the following characteristics:

1. 'Tanlilida' has more flower petals than 'POULfl001'.
2. Sepals of 'POULfl001' have more prominent foliaceous appendages than those of 'Tanlilida'.

The new variety may be distinguished from its pollen parent, by the following combination of characteristics:

1. 'POULfl001' has more flower buds per flowering stem than the pollen parent.
2. 'POULfl001' has a darker red flower color than that of the pollen parent plant.

The objective of the hybridization of this rose variety was to create a new and distinct variety for garden use with unique qualities, such as:

1. Uniform and abundant clusters of red flowers;
2. Vigorous, but compact growth when propagated both as a budded rose and on its own roots;
3. Disease resistance;
4. Continuous flowering.

This combination of qualities is not present in previously available commercial cultivars of this type, known to the inventors, and distinguish 'POULfl001' from all other varieties of which we are aware.

As part of their rose development program, L. Pernille Olesen and Mogens N. Olesen germinated the seeds from the aforementioned hybridization during winter of 1991 and conducted evaluations on the resulting seedlings in a controlled environment in Fredensborg, Denmark.

'POULfl001' was selected in the spring 1992 by the inventors as a single plant from the progeny of the aforementioned hybridization.

Asexual reproduction of 'POULfl001' by traditional budding and rooted cuttings was first done by L. Pernille and Mogens N. Olesen in their nursery in Fredensborg, Denmark in July, 1992. This initial and other subsequent asexual propagations conducted in controlled environments have demonstrated that the characteristics of 'POULfl001' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULfl001'. Specifically illustrated in FIG. 1:

FIG. 1.1; Open flower, stem showing open flower, branching, and the attachment of leaves, buds, and peduncles;

FIG. 1.2; Flower bud closed, flower bud as sepals unfold, and partially open;

FIG. 1.3; Sepals, receptacle, and peduncle;

Specifically illustrated in FIG. 2:

FIG. 2.1; Flower petals, detached;

FIG. 2.2; Juvenile stem exhibiting anthocyanin and mature stem;

FIG. 2.3; Mature leaf.

DETAILED DESCRIPTION OF THE VARIETY

The following is a description of 'POULfl001', as observed in its growth in a field nursery in Jackson County, Oreg. Observed plants are 3 years of age. Plants were grown on *Rosa multiflora* understock. Color references are made using The Royal Horticultural Society (London, England) Colour Chart, 1995, except where common terms of color are used.

For a comparison, several physical characteristics of the rose variety 'POULcs001', a rose variety from the same inventors described and illustrated in U.S. Plant patent application Ser. No. 10/336,058 dated Jan. 3, 2003 (now abandoned) are compared to 'POULfl001' in Chart 1.

CHART 1

| | 'Poulf1001' | 'POULcs001' |
|---|---|---|
| General tonality | Red Group 46A | Red Group 46A |
| Petalage | 30 petals | 24 to 26 petals |
| Compound leaf size | 200 mm long by 100 mm wide | 130 mm (1) × 80 mm (w) |
| Diameter of open flower | 85 mm | 65 to 70 mm |

FLOWER AND FLOWER BUD

Blooming habit: Continuous.

Flower bud:

*Size.*—Upon opening, 28 mm in length from base of receptacle to end of bud. Bud diameter is 18 mm on average.

*Bud form.*—Pointed ovoid with broad base.

*Bud color.*—As sepals unfold, petals are Red Group 53A. At ¼ opening petals are Red Group 46A.

*Sepals.*—Upper surface: Color: Yellow-Green Group 144A. Abundant anthocyanin the color of Greyed-Red Group 178A observed. Surface: Surfaces of sepals are moderately pubescent. Lower surface: Color: Yellow-Green Group 144A. Anthocyanic pigmentation the color of Greyed-Red Group 178A observed. Texture: Smooth with stipitate glands. Sepal shape: Sepal apex is cirrhose. Base is flat at union with receptacle. Sepal margin: Margins have strong foliaceous appendages on three of the five sepals. Stipitate glands present in medium quantity. Size: 35 mm (l)×7 mm (w).

*Receptacle.*—Surface: Smooth and glabrous. Shape: Urn-shaped. Size: 6 mm (h)×7 mm (w). Color: Yellow-Green Group 144A. Anthocyanic pigments the color of Greyed-Red Group 178A observed.

*Peduncle.*—Surface: Somewhat rough due to the presence of stipitate glands. Length: 55 to 65 mm. Color: Yellow-Green Group 144B. Strong anthocyanic pigmentation the color of Greyed-Red Group 178A observed. Strength: Somewhat weak.

*Borne.*—In clusters of 12 flower buds per stem.

Flower bloom:

*Fragrance.*—Light rose scent.

*Duration.*—The blooms have a duration on the plant an average of 10 days. After flowers have completely matured petals fall cleanly away from plant.

*Size.*—Flower diameter averages 85 mm when fully open. Flower depth ranges from 35 to 40 mm.

*Form.*—Generally flowers are cupped with many slightly overlapping petals. Shape of flower when viewed from the side: Upon opening, upper part: Flat. Upon opening, lower part: Flat. Open flower, upper part: Flattened convex. Open flower, lower part: Convex.

*Petalage.*—On average 30 petals under normal conditions with 7 petaloids.

Color:

Upon opening, petals:

*Outermost petals.*—Outer side: Red Group 53C. Inner side: Red Group 46B.

*Innermost petals.*—Outer side: Red Group 53C. Inner side: Red Group 46B.

Upon opening, basal petal spots:

*Outermost petals.*—Outer side: White Group 155A with intonations of Yellow Group 12C. Inner side: White Group 155A with intonations of Yellow Group 12C.

*Innermost petals.*—Outer side: White Group 155A with intonations of Yellow Group 12C. Inner side: White Group 155A with intonations of Yellow Group 12C.

After opening, petals:

*Outermost petals.*—Outer side: Red Group 53C. Inner side: Red Group 46B.

*Innermost petals.*—Outer side: Red Group 53C. Inner side: Red Group 46B.

After opening, basal petal spots:

*Outermost petals.*—Outer side: White Group 155A with intonations of Yellow Group 12C. Inner side: White Group 155A with intonations of Yellow Group 12C.

*Innermost petals.*—Outer side: White Group 155A with intonations of Yellow Group 12C. Inner side: White Group 155A with intonations of Yellow Group 12C.

General tonality: On open flower Red Group 46A. No change in the general tonality at the end of the $10^{th}$ day. Afterwards, general tonality is Red Group 46A with intonations of Red-Purple Group 61B.

Petals:

*Petal reflex.*—Petals are slightly reflexed and have a ruffled appearance.

*Margin.*—Entire and uniform. Weak undulations of margin observed.

*Shape.*—Apex: Round. Base: Acute.

*Size.*—14 mm (l)×11 mm (w).

*Texture.*—Smooth.

*Thickness.*—Average.

*Arrangement.*—Not Formal.

Petaloids:

*Quantity.*—5 to 8.

*Color.*—Upper surface: Red Group 46B. Lower surface: Red Group 53C.

Reproductive organs:

*Pistils.*—Length: 7 mm. Quantity: 53 (actual count).

*Pollen.*—Color: Yellow Group 13A. Quantity: Average.

*Anthers.*—Size: 1 to 2 mm in length. Color: Yellow Group 13A. Quantity: 90 (actual count).

*Filaments.*—Color: Yellow Group 8A. Length: 4 mm.

*Stigmas.*—Superior, relative to the length of the filaments and the height of the anthers. Color: Greyed-Yellow Group 161C.

*Styles.*—Color: Greyed-Yellow Group 161C. Other intonations observed are Greyed-Red Group 180C.

*Hips.*—None Observed in the field nursery in Jackson County Oreg.

PLANT

Plant growth: Moderate, upright to bushy. When grown as a budded field grown plant on *Rosa multiflora* understock, the height of the plant ranges from 60 to 100 cm and the average width is 65 cm.

Stems:

*Color.*—Young wood: Yellow-Green Group 144B with intonations of Greyed-Red Group 178A. Older wood: Green Group 137C to Yellow-Green Group 144A.

*Surface texture.*—Young wood: Smooth. Older wood: Rough.

Thorns:

*Incidence.*—1 to 2 thorns per 10 cm of stem.

*Size.*—Average length is 5 mm.

*Color.*—Greyed-Red Group 178A.

*Shape.*—Deeply concave.

Plant foliage: Normal number of leaflets on normal leaves in middle of the stem: 7 leaflets.

*Compound leaf size.*—200 mm (l)×100 mm (w).

*Color of mature foliage.*—Upper surface; Yellow-Green Group 147A. Lower surface: Yellow-Green Group 147B.

*Color of juvenile foliage.*—Upper surface: Yellow-Green Group 144C with strong intonations of Greyed-Purple Group 183C. Lower surface: Greyed-Purple Group 183C. Anthocyanin: Location: Juvenile stems and foliage. Color: Greyed-Purple Group 183C.

Plant leaves and leaflets:

*Stipules.*—Size: 25 mm in length. Shape: Linear with outward extending apecies. Quantity: 2 per compound leaf. Margins: Serrated, with abundant stipitate glands. Color: Yellow-Green Group 144A. Anthocyanin at margins is Greyed-Purple Group 183C.

*Petiole.*—Length: 35 mm on average. Above: Color: Yellow-Green Group 144B. Anthocyanin: Greyed-Purple Group 183A. Underneath: Smooth.

*Rachis.*—Length: 120 to 130 mm. Color: Yellow-Green Group 144B. Anthocyanic pigments the color of Greyed-Purple Group 183C observed.

*Leaflet.*—Edge: Serrated. Size: 70 mm (l)×64 mm (w). Shape: Ovate to round. Base shape is rounded. Apex shape is mucronate. Texture: Smooth. Thickness: Average. Arrangement: Odd pinnate. Venation: Reticulate. Glossiness: Moderately glossy.

Disease resistance: Above average resistance to mildew, rust, black spot, and *Botrytis* under normal growing conditions in Jackson County, Oreg.

Cold hardiness: The variety 'POULfl001' has been found to be cold tolerant to USDA Cold Hardiness Zone 6.

It is claimed:

1. A new and distinct variety of rose plant of the floribunda rose class named 'POULfl100', substantially as herein illustrated and described as a distinct and novel rose variety due to its abundant red flowers, disease resistance, and extended period of bloom.

* * * * *

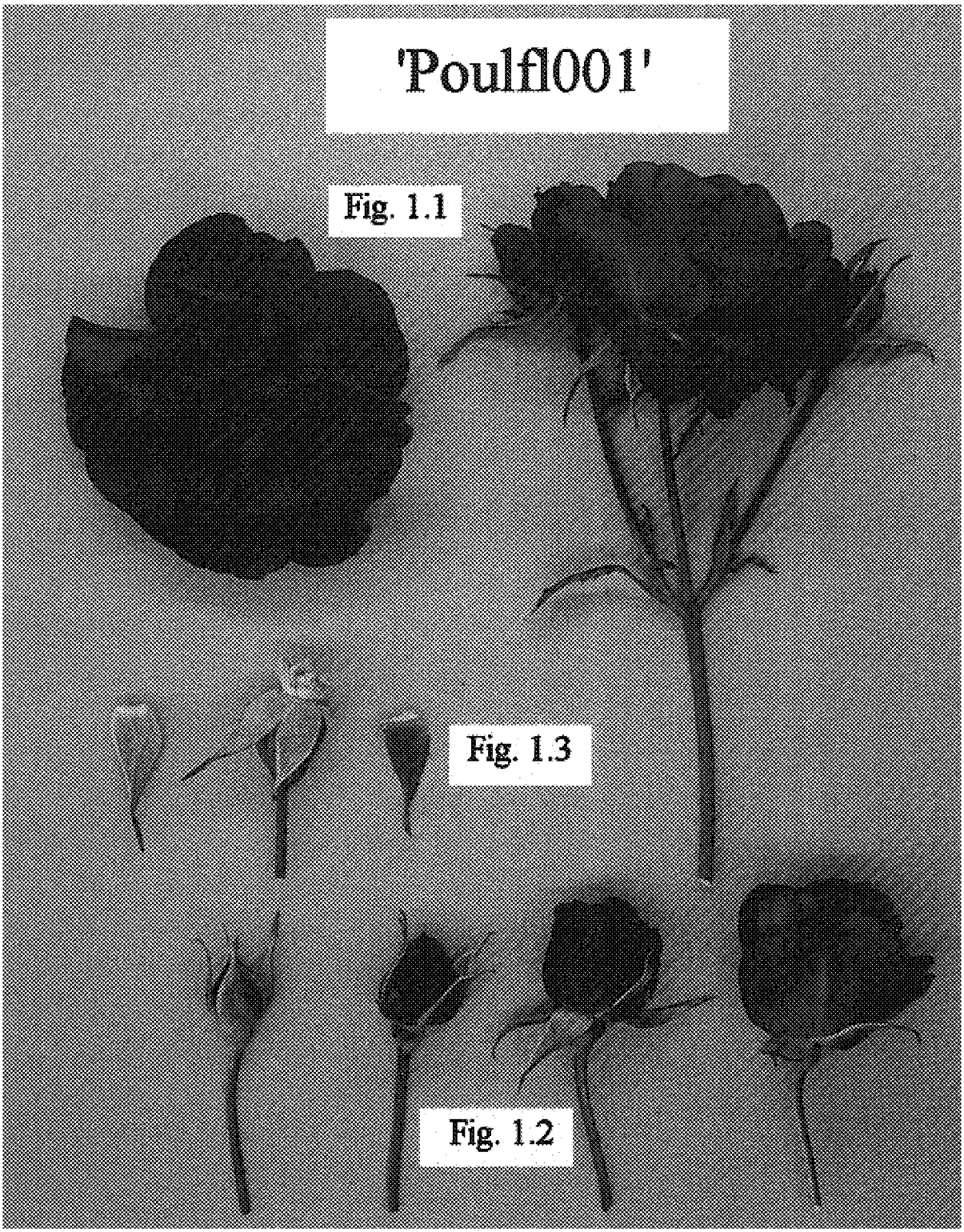
'Poulfl001'
Fig. 1.1
Fig. 1.3
Fig. 1.2

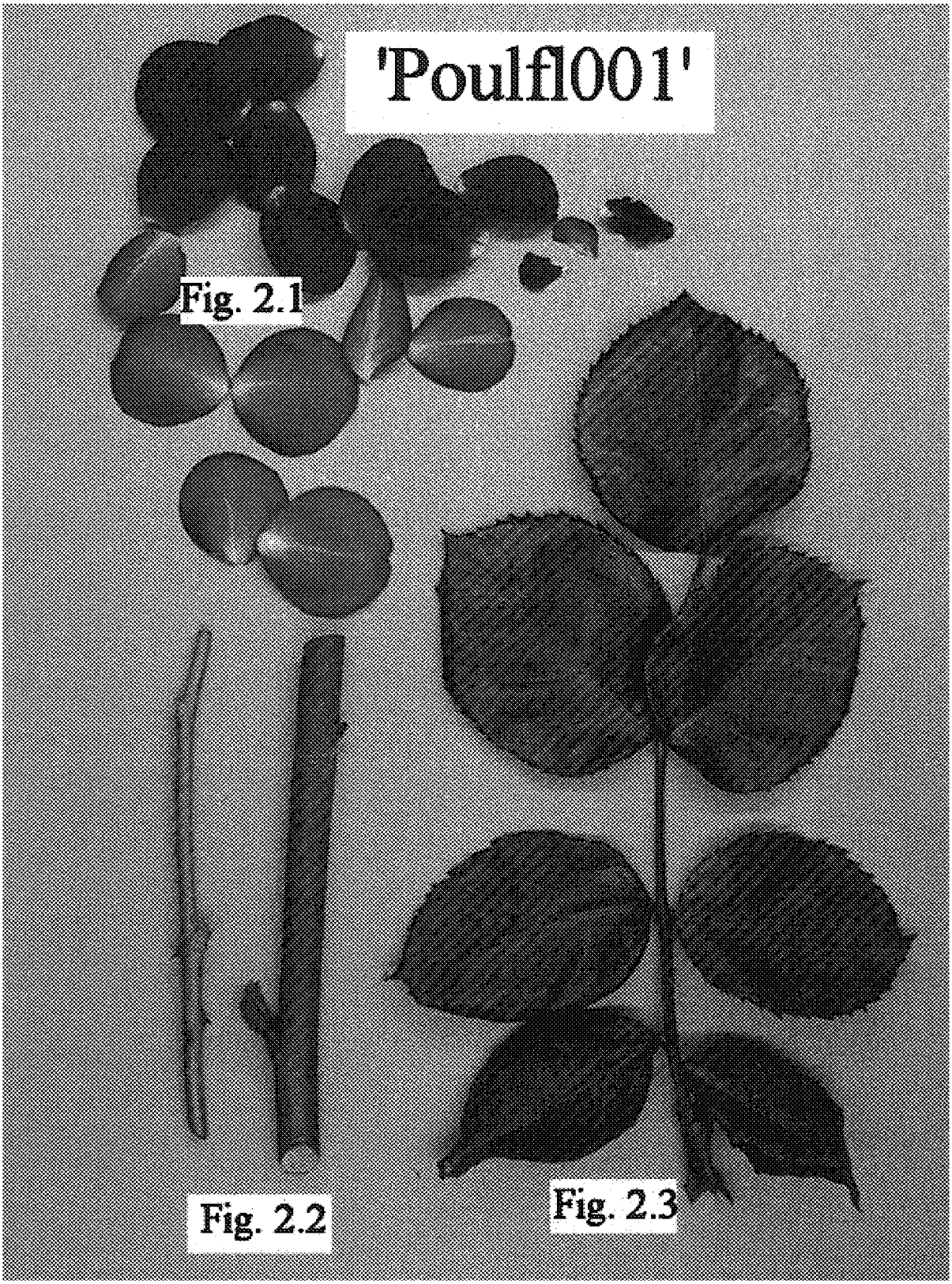
'Poulfl001'
Fig. 2.1
Fig. 2.2
Fig. 2.3